United States Patent
Schindele

(10) Patent No.: US 6,891,681 B2
(45) Date of Patent: May 10, 2005

(54) ANTI-GLARE PROTECTION DEVICE

(75) Inventor: Ronald Schindele, Gossau (CH)

(73) Assignee: Optrel AG, Wattil (CH)

( * ) Notice: Subject to any disclaimer, the term of this patent is extended or adjusted under 35 U.S.C. 154(b) by 0 days.

(21) Appl. No.: 10/257,747

(22) PCT Filed: Apr. 3, 2001

(86) PCT No.: PCT/CH01/00213
§ 371 (c)(1),
(2), (4) Date: Jun. 16, 2003

(87) PCT Pub. No.: WO01/81819
PCT Pub. Date: Nov. 1, 2001

(65) Prior Publication Data
US 2004/0083539 A1 May 6, 2004

(30) Foreign Application Priority Data
Apr. 22, 2000 (CH) ................................................ 794/00

(51) Int. Cl.$^7$ ...................... G02B 13/20; G02B 26/00; G02F 1/1335; A61F 9/00
(52) U.S. Cl. ...................... 359/707; 359/238; 359/265; 349/14; 2/8
(58) Field of Search ................................ 359/707, 238, 359/265, 275, 722, 723; 349/14, 142, 149, 58; 2/8

(56) References Cited

U.S. PATENT DOCUMENTS

| 2,152,383 | A | | 3/1939 | Leader ............................... 2/8 |
| 5,042,821 | A | | 8/1991 | Bontly ........................ 359/513 |
| H000975 | H | * | 11/1991 | Selkowitz et al. ............. 52/172 |
| 5,522,006 | A | * | 5/1996 | Takeuchi et al. ............. 385/139 |
| 5,959,705 | A | | 9/1999 | Fergason ...................... 349/14 |
| 6,299,199 | B1 | * | 10/2001 | Bowers et al. ........... 280/730.2 |
| 6,369,935 | B1 | * | 4/2002 | Cardinal et al. ............. 359/265 |

* cited by examiner

Primary Examiner—Timothy Thompson
(74) Attorney, Agent, or Firm—Rankin, Hill, Porter & Clark LLP

(57) ABSTRACT

An anti-glare protection device, for example a pair of welding goggles, a welding mask or a welding helmet, includes a supporting part with a sight opening (3), an optical filter element arranged in the sight opening, and a protective plate (1), which is mounted or can be mounted on the supporting part such covering the optical filter element. For the protection of the filter element against contamination with dirt and in order to protect the wearer of the anti-glare protection device against undesirable gases, smoke and dirt, a seal (4) made out of an elastically compressible material is disposed either between the supporting part and the protective plate (1) or between the filter element and the protective plate (1). The seal extends substantially around the sight opening and is advantageously affixed either to the supporting part, to the protective plate (1), or to the filter element.

5 Claims, 1 Drawing Sheet

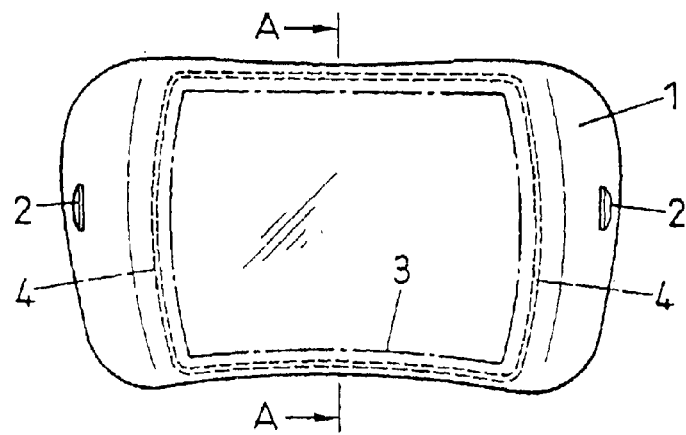
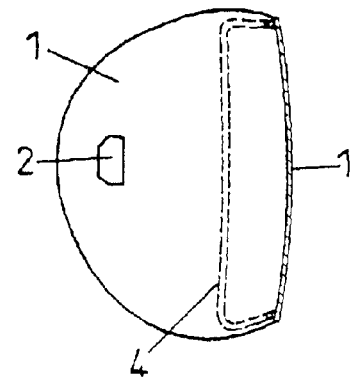
FIG. 1
FIG. 2
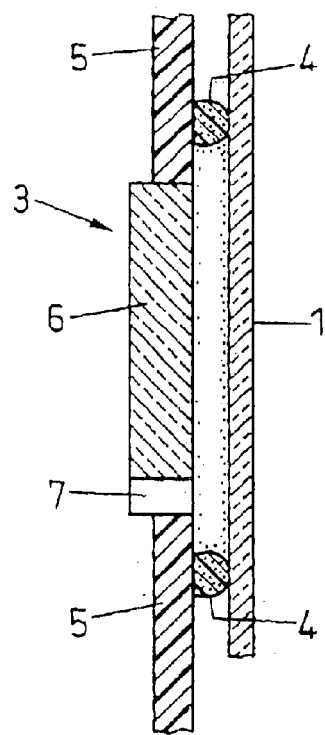
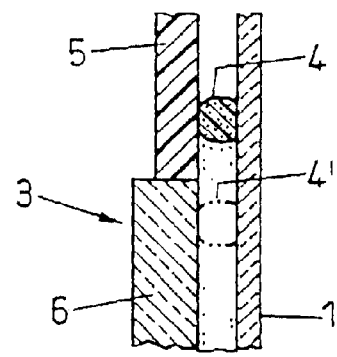
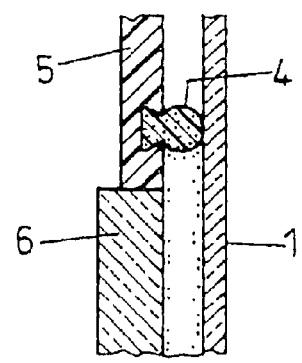
FIG. 3
FIG. 4
FIG. 5

ANTI-GLARE PROTECTION DEVICE

BACKGROUND OF THE INVENTION

1. Field of the Invention

The invention relates to an anti-glare protection device and, more particularly, toward an anti-glare protection device that is used on a pair of welding goggles, a welding mask, or a welding helmet and comprises a supporting part with a sight opening, a protective plate covering the sight opening, and an optical filter element arranged behind the protective plate.

2. Description of Related Art

A supporting part of welding goggles, welding masks or welding helmets, apart from its supporting function, serves to protect the welder against mechanical influences and against heat radiation. This supporting part usually consists of a plastic material, for example, of poly-carbonate and is manufactured by injection molding or by press molding.

The filter element is arranged in the sight opening of the supporting part and serves as optical protection for the wearer and, therefore, represents the actual anti-glare protection of the device. The filter element may be passive, i.e. it for example may consist of Wood's glass. The filter element, however, may also be active such that it blocks or reduces the passage of light when the external light intensity exceeds a predefined threshold value. An opto-electronic element in the form of at least one liquid-crystal cell (liquid-crystal cell or LC-cell) may be serving as active filter element. An optical sensor for detecting the external light intensity is also installed in the sight opening. Suitable means are provided for processing the measuring signal of the sensor into control signals for controlling the optical transmittance of the filter element.

The protective plate covers the sight opening of the supporting part such that the filter element and, if so required, the optical sensor are positioned behind the protective plate, i.e., when worn between the protective plate and the eyes of the welder. The protective element is transparent and it serves to protect the optical filter element from soiling and damage. The protective plate advantageously consists of a plastic material such as poly-carbonate, and is mounted on the supporting part in either a fixed or interchangeable manner. For this mounting, the supporting part and/or the protective plate are usually equipped with connecting means such that the protective plate can be installed by, for example, snapping-in and such that, when installed, is more or less pressed against the supporting part or is tensioned together with it.

It becomes manifest that filter elements and sensors necessary for active filter elements of anti-glare protection devices, even if they are protected towards the outside by the protective plate, get contaminated with dirt relatively quickly and consequently lose their functional security. It also becomes manifest that an additional protection of the wearer against smoke and gases generated during welding would be desirable.

SUMMARY OF THE INVENTION

The invention is directed toward creating an anti-glare protection device comprising a supporting part, a protective plate and an optical filter element arranged behind the protective plate, which anti-glare protection device provides, with a minimum additional manufacturing effort, a better protection of the filter element and, in the case of an active filter element, a better protection of the sensor belonging to the active filter element, and simultaneously provides an enhanced protection of the wearer against gases, smoke and dirt than is possible with corresponding devices in accordance with prior art.

The anti-glare protection device according to the invention comprises a seal between the supporting part and the protective plate or between the filter element and the protective plate. The seal extends around the sight opening, and prevents contamination with dirt and undesirable gases inside the anti-glare protection device to a high degree. The seal, therefore, represents a very simple, but nonetheless very effective, improvement of known anti-glare protection devices.

The seal of the anti-glare protection device in accordance with the invention consists of an elastically compressible material and is dimensioned such that the protective plate lies gastight against the supporting part or against the filter element in every condition of the anti-glare protection device. Furthermore, the seal has a shock-absorbing effect such that the protective plate is able to survive mechanical influences, such as blows, without suffering damage.

In an anti-glare protection device according to the prior art, the protective plate being snapped-on may also lie against the supporting part. In no way, however, is the protective plate lying against the supporting part so as to be gastight. Therefore, the difference between the anti-glare protection device according to the invention and a corresponding known anti-glare protection device consists in an elastically compressible seal, which is arranged around the sight opening between the protective plate and the supporting part or between the protective plate and the filter element, and which is designed for substantially preventing the ingress of gas behind the protective plate not only in a new and unloaded condition of the anti-glare protection device, but also in a used condition (i.e. having been subjected to distorting wear) and, furthermore, also while being worn, i.e. when the supporting part may be displaced relative to the protective plate or may be warped by mechanical or thermal stress.

Advantageously, the seal is affixed to the supporting part, to the filter element or to the protective plate and consists of plastic material, advantageously foamed polyurethane or a suitable silicone plastic material.

BRIEF DESCRIPTION OF THE DRAWINGS

These and further features of the invention will be apparent with reference to the following description and drawings, wherein:

FIGS. 1 and 2 show an interchangeable protective plate for a pair of welding goggles, for a welding mask or for a welding helmet, on which protective plate a seal is affixed (FIG. 1: front view; FIG. 2: section A—A);

FIGS. 3 to 5 show three exemplary embodiments of seals of the anti-glare protection device in accordance with the invention.

DETAILED DESCRIPTION OF THE PREFERRED EMBODIMENTS

FIGS. 1 and 2 illustrate an exemplary protective plate 1 for an anti-glare protection device according to the invention. FIG. 1 is a front view of the plate, while FIG. 2 is a section as seen along line A—A of FIG. 1. The protective plate is laterally arched towards the rear and comprises lateral slits 2, with the help of which the protective plate is affixed, e.g. snapped onto a supporting part (not illustrated). FIG. 1 shows the contour of the sight opening 3 of the supporting part as a dot-dash line. A seal 4 extends around this sight opening 3, the seal being affixed to the protective plate.

FIG. 3 illustrates as a detail a section through protective plate 1, supporting part 5 with sight opening 3 and through a filter element 6 with sensor 7 arranged in the sight opening. The seal 4 is visible between the protective plate 1 and the supporting part 5. The seal 4 is, in the illustrated case, affixed to the supporting part 5.

FIG. 4 depicts a similar section as FIG. 3, wherein the seal 4' represented in this case is affixed to the protective plate 1. With a dot-dash line, the seal 4' is also illustrated in a position in which it is not arranged between the supporting part 5 and the protective plate 1, but rather is disposed between the optical filter element 6 and the protective plate 1. Also in this case, the seal 4' substantially extends around the sight opening 3 of the supporting part 5, i.e. substantially parallel to the edge of the sight opening 3.

Advantageously a seal 4, as illustrated in FIGS. 3 and 4, is manufactured by extruding the plastic material for the seal in a foamed state directly onto the supporting part 5 or onto the protective plate 1, respectively, or on to the filter element 6. In this manner, a direct material-to-material connection to the plastic material of the supporting part 5, the protective plate 1, or the filter element 6 is produced. This connection is similar to one produced by welding or gluing and through this connection the seal 4 is absolutely adequately connected with the supporting part 5, protective plate 1, or filter element 6.

FIG. 5 illustrates a further embodiment of a seal 4 being fixed in a corresponding groove of the supporting part 5 by a positive form fit. This seal may be a commercially available O-ring. Such a seal may also be arranged on the protective plate 1 or on the filter element 6 instead of on the supporting part 5.

What is claimed is:

1. An anti-glare protection device comprising a supporting part (5), an active optical filter element (6) arranged within a sight opening (3) of the supporting part (5) and with a transmittance being controlled by an optical sensor (7), and a protective plate (1) affixable to the supporting part (5) so as to cover the optical filter element (6) and the sensor (7), wherein, for protecting the filter element (6) and the sensor (7) against gases, smoke and dirt, a seal (4, 4') substantially extending around the sight opening (3) and the sensor (7) is disposed between one of the supporting part (5) and the protective plate (1) or the filter element (6) and the protective plate (1), the seal consisting of an elastically compressible material and being affixed to only one of the supporting part (5), the protective plate (1) or the optical filter element (6) and rendering reducing a flow of gas therepast.

2. The anti-glare protection device in accordance with claim 1, wherein the seal (4) is affixed with one of a direct material to material connection or a positive form fit.

3. The anti-glare protection device according to claim 1, wherein the seal is formed from a foamed plastic material.

4. The anti-glare protection device according to claim 1, wherein the seal (4) is formed from a material selected from the group consisting of polyurethane and silicone plastic.

5. The anti-glare protection device according to claim 1, wherein the filter element (6) comprises at least one liquid crystal element and means for controlling the at least one liquid crystal element based upon a signal from the optical sensor (7).

* * * * *